(12) United States Patent
Luo et al.

(10) Patent No.: US 9,850,205 B2
(45) Date of Patent: Dec. 26, 2017

(54) STABLE APREMILAST CRYSTALLINE FORM II FREE OF SOLVATE AND METHOD OF MAKING THE SAME

(71) Applicants: UTOPHARM (SHANGHAI) CO., LTD, Shanghai (CN); Junzhi Luo, Shanghai (CN)

(72) Inventors: Junzhi Luo, Shanghai (CN); Jing Nian, Shanghai (CN); Siyuan Gao, Shanghai (CN)

( * ) Notice: Subject to any disclaimer, the term of this patent is extended or adjusted under 35 U.S.C. 154(b) by 0 days.

(21) Appl. No.: 15/638,384

(22) Filed: Jun. 30, 2017

(65) Prior Publication Data

US 2017/0298018 A1  Oct. 19, 2017

Related U.S. Application Data

(63) Continuation of application No. PCT/CN2015/000566, filed on Aug. 5, 2015.

(30) Foreign Application Priority Data

Mar. 7, 2015  (CN) .......................... 2015 1 0101009

(51) Int. Cl.
*A61K 31/40* (2006.01)
*C07D 209/46* (2006.01)
*A61K 31/4035* (2006.01)
*G01N 25/48* (2006.01)
*G01N 23/20* (2006.01)
*G01N 21/35* (2014.01)

(52) U.S. Cl.
CPC ........ *C07D 209/46* (2013.01); *A61K 31/4035* (2013.01); *G01N 23/2005* (2013.01); *G01N 25/4866* (2013.01); *G01N 2021/3595* (2013.01)

(58) Field of Classification Search
None
See application file for complete search history.

(56) References Cited

U.S. PATENT DOCUMENTS

2008/0234359 A1* 9/2008 Muller ............... A61K 31/4035
514/417

FOREIGN PATENT DOCUMENTS

| CN | 102046167 A | 5/2011 |
|---|---|---|
| CN | 104761484 A | 7/2015 |
| CN | 104496886 A | 9/2016 |

* cited by examiner

*Primary Examiner* — Sreeni Padmanabhan
*Assistant Examiner* — Jeanmarie Calvillo
(74) *Attorney, Agent, or Firm* — Wayne & Ken, LLC; Tony Hom

(57) ABSTRACT

A stable Crystalline Form II of non-solvate of Apremilast (Formula I), methods of making Form II, pharmaceutical compositions comprising Form II, and their uses are disclosed. Also discloses are mixed crystals comprising Form Hand Form B and methods of making the same. The crystalline forms are characterized using X-ray powder diffractometry (XRPD), infrared spectroscopy (IR), differential scanning calorimetry (DSC), and thermal gravimetric analysis (TG). As compared with Forms A, B, C, D, E, F, and G reported in prior art references, Apremilast Form II of the present invention is more stable to temperature, light, and humidity, and is more suitable for long term storage; the crystallization solvents are safe and can be easily removed; the Form II has a white or off white appearance, and can be directly used in preparation processing; the preparation methods are simple and easy to reproduce, and are suitable for industrialized production.

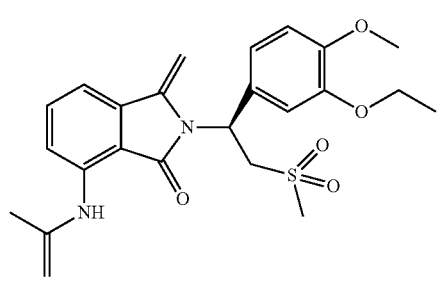

10 Claims, 23 Drawing Sheets

STABLE APREMILAST CRYSTALLINE FORM II FREE OF SOLVATE AND METHOD OF MAKING THE SAME

FIELD OF THE INVENTION

The present invention relates to Apremilast Crystalline Form II, in particular Crystalline Form II of phosphodiesterases 4 (PDE4) inhibitor Apremilast, pharmaceutical compositions comprising the same, methods of making the same, and use of the crystalline form in treating various diseases and disorders. The present invention is in the field of pharmaceutical chemistry.

BACKGROUND OF THE INVENTION

It is well known in the art that different crystalline forms can be obtained due to the differences in crystallization solvents and methods, e.g., crystallization temperature, cooling rate, stirring or standing, and that different crystalline forms may have different stability and solubility, sometimes even different in vivo bioavailability. Accordingly, it is necessary to obtain a crystalline form with high purity and is thermodynamically stable in the development of a drug, and the method of making the crystalline form may be easily reproduced and is suitable for industrial scale preparation. In addition, X-ray powder diffractometry(XRPD), infrared spectroscopy (IR), differential scanning calorimetry(DSC), and thermal gravimetric analysis (TG) are effective means of characterizing crystalline forms.

Apremilast (Compound I, chemical name is (+)-2-[1-(3-ethoxy-4-methoxyphenyl)-2-methylsulfonylethyl]-4-acetylaminoisoindoline-1,3-dione) is a phosphodiesterases 4 (PDE4) inhibitor which acts on Adenosine 3',5'-cyclic monophosphate (cAMP), wherein inhibition of PDE4 can result in increased intracellular cAMP levels, thereby alleviating arthrocele and improving the physiological function of joints. The structure of Apremilast is shown below:

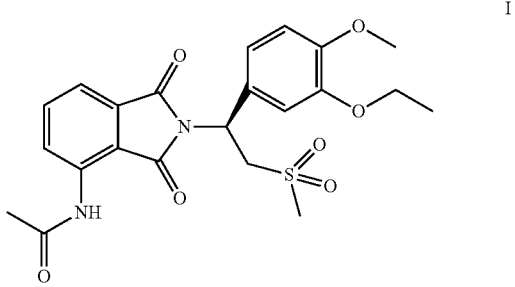 [SMILES: CCOc1cc([C@@H](CS(C)(=O)=O)N2C(=O)c3cccc(NC(C)=O)c3C2=O)ccc1OC]

This drug has been approved for treating psoriatic arthritis in US in March 2014 and approved for treating psoriasis in September of the same year. Crystalline forms of the drug have been reported in CN102702070A; this patent disclosed seven solid forms or crystalline forms of Apremilast, namely Forms A, B, C, D, E, F, and G, the XRPD patterns, DSC patterns, and TGA patterns of said forms are summarized in Table 1 below.

Amongst the crystalline forms, Forms C, D, E, and G are solvates and are not suitable for use in medicine; Forms A, B, and F are non-solvates or substantially free of solvents. This patent disclosed the conversion between different crystalline forms, but did not provide any working example of preparing each crystalline form, thus cannot be reproduced.

TABLE 1

Data of Apremilast crystalline forms reported in CN102702070A

| Solid forms | Crystallization solvents and methods | Characterizing XRPD peaks | DSC pattern | TGA pattern |
| --- | --- | --- | --- | --- |
| A | Acetone, ethyl alcohol or their combination, rapid cooling and crystallization | 8.1, 14.4, 15.2, 17.4, 18.4, 19.2, 20.5, 22.8, 23.2, 23.6, 24.5, 25.1 | 147° C. 158° C. | 0.05% |
| B | isopropanol, acetone, acetonitrile, ethyl alcohol, ethyl acetate, heptane, methanol, butanone, methyl tertiary butyl ether, dichloromethanen-butyl alcohol, n-butyl acetate, THF, toluene, water, or acetone + ethyl alcohol, ethyl alcohol + water | 10.1, 12.4, 13.5, 15.7, 16.3, 18.1, 20.7, 22.5, 24.7, 26.2, 26.9, 29.1 | 157° C. | 0.25% |
| C | acetone, acetonitrile, ethyl alcohol, heptane, methanol, butanone, THF, toluene, water or a combination of two or more of the above solvents; | 7.5, 11.3, 15.3, 16.4, 17.8, 21.4, 22.6, 23.5, 24.8, 25.5, 26.4, 27.6 | 153° C. 187° C. | 5.95% toluene solvate |
| D | dichloromethane | 7.5, 9.6, 11.3, 13.9, 16.3, 17.7, 20.5, 23.2, 24.6, 25.2, 26.0, 28.8 | 104° C. | 6.5% dichloro methane solvate |
| E | acetone, acetonitrile, heptane, dichloromethane, or a combination of two or more of the above solvents; | 7.6, 9.2, 11.4, 15.5, 16.5, 17.9, 19.6, 20.5, 21.6, 22.8, 23.8, 26.6 | 100° C. | 4.0%, acetonitrile solvate |
| F | ethyl alcohol, acetone, water, or a combination of two or more of the above solvents; | 8.1, 8.6, 15.6, 17.3, 19.3, 21.4, 22.8, 24.6, 25.4, 25.9, 26.6 | 149° C. | 0.06% |
| G | ethyl acetate | 7.9, 9.5, 11.7, 15.7, 16.8, 18.1, 19.7, 21.8, 22.8, 25.1, 25.8, 26.7 | 112° C. | 3.62%, ethyl acetate solvate |

Amongst the Forms A, B, C, D, E, F, and G disclosed in CN102702070A and the registration file submitted to the EMEA by Celgene, it is believed that Form B is the most thermodynamically stable form, which is suitable for storage and preparation processing. However, Otezla, which is sold by Celgene, has a shelf life of merely one year, which is a disadvantage for a commercial product. Thus, there is the need to obtain a more thermodynamically stable crystalline form that is suitable for long term storage of the API and preparations, and said crystalline form does not affect the in vivo bioavailability, or even has a better in vivo bioavailability than the known crystalline forms.

DESCRIPTION OF THE INVENTION

The present invention provides a novel and stable Crystalline Form II of non-solvate of Apremilast, compositions comprising the same and applications therefor. The present invention also provides simple methods of making the Apremilast Crystalline Form II which are suitable for industrial. In addition, the present invention provides methods of making mixed crystals of Apremilast, i.e., methods of making mixed crystals of Apremilast comprising Apremilast Crystalline Form II and Apremilast Crystalline Form B.

More importantly, Apremilast Crystalline Form II of the present invention is more thermodynamically stable than the known crystalline forms of Apremilast, such as Forms A, B, C, D, E, F or G.

In certain aspects, Apremilast Crystalline Form II of the present invention has better in vivo bioavailability than the known Apremilast Crystalline Form B.

CN201410335852.6 relates to methods of preparing Apremilast and its intermediates; CN201410420960.3 relates to a stable Crystalline Form I of non-solvate of Apremilast and methods of making the same, both of which are incorporated by reference herein.

The Crystalline Form II of non-solvate of Apremilast of the present invention is characterized in that:

A Crystalline Form II of non-solvate of Apremilast of Formula (I),

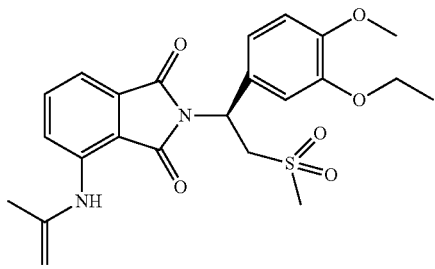

I wherein it has an X-ray powder diffraction pattern (XRPD) comprising the following exemplary characterizing absorption peaks at 2θ±0.2:

| # | 2-Theta | d (A) | Height | I% | Area | I% | FWHM |
|---|---------|-------|--------|------|-------|-------|-------|
| 1 | 10.666 | 8.2876 | 568 | 10.9 | 1090 | 2.4 | 0.077 |
| 2 | 11.290 | 7.8312 | 3576 | 68.5 | 45434 | 100.0 | 0.234 |
| 3 | 12.573 | 7.0346 | 833 | 15.9 | 2789 | 6.1 | 0.111 |
| 4 | 13.203 | 6.7001 | 3140 | 60.1 | 31411 | 69.1 | 0.192 |
| 5 | 13.541 | 6.5338 | 2509 | 48.0 | 22813 | 50.2 | 0.174 |
| 6 | 13.874 | 6.3775 | 1946 | 37.3 | 17299 | 38.1 | 0.193 |
| 7 | 14.724 | 6.0114 | 5224 | 100.0 | 42800 | 94.2 | 0.149 |
| 8 | 16.223 | 5.4592 | 2582 | 49.4 | 21876 | 48.1 | 0.163 |
| 9 | 17.924 | 4.9448 | 2862 | 54.8 | 24450 | 53.8 | 0.164 |

-continued

| # | 2-Theta | d (A) | Height | I% | Area | I% | FWHM |
|---|---------|-------|--------|------|-------|-------|-------|
| 10 | 18.751 | 4.7285 | 2068 | 39.6 | 15517 | 34.2 | 0.153 |
| 11 | 20.290 | 4.3731 | 1268 | 24.3 | 7487 | 16.5 | 0.139 |
| 12 | 20.725 | 4.2822 | 832 | 15.9 | 3836 | 8.4 | 0.143 |
| 13 | 21.531 | 4.1238 | 1573 | 30.1 | 8335 | 18.3 | 0.132 |
| 14 | 21.989 | 4.0388 | 1666 | 31.9 | 18358 | 40.4 | 0.277 |
| 15 | 22.778 | 3.9007 | 1887 | 36.1 | 19298 | 42.5 | 0.244 |
| 16 | 23.194 | 3.8317 | 1404 | 26.9 | 19738 | 43.4 | 0.375 |
| 17 | 25.265 | 3.5221 | 1412 | 27.0 | 22193 | 48.8 | 0.382 |
| 18 | 25.641 | 3.4714 | 1702 | 32.6 | 19926 | 43.9 | 0.268 |
| 19 | 26.587 | 3.3499 | 1904 | 36.4 | 20529 | 45.2 | 0.244 |
| 20 | 27.022 | 3.2970 | 3644 | 69.8 | 44458 | 97.9 | 0.234 |
| 21 | 27.596 | 3.2297 | 962 | 18.4 | 5166 | 11.4 | 0.194 |
| 22 | 28.226 | 3.1590 | 1147 | 22.0 | 7133 | 15.7 | 0.170 |
| 23 | 29.112 | 3.0648 | 581 | 11.1 | 973 | 2.1 | 0.103 |
| 24 | 29.667 | 3.0087 | 463 | 8.9 | 696 | 1.5 | 0.133 |
| 25 | 30.934 | 2.8884 | 482 | 9.2 | 1767 | 3.9 | 0.207 |
| 26 | 32.035 | 2.7916 | 486 | 9.3 | 1075 | 2.4 | 0.150 |
| 27 | 33.023 | 2.7103 | 450 | 8.6 | 1343 | 3.0 | 0.215 |
| 28 | 33.597 | 2.6653 | 473 | 9.1 | 2192 | 4.8 | 0.261 |
| 29 | 34.207 | 2.6191 | 509 | 9.7 | 2957 | 6.5 | 0.263 |
| 30 | 34.915 | 2.5676 | 404 | 7.7 | 1621 | 3.6 | 0.275 |
| 31 | 36.222 | 2.4779 | 336 | 6.4 | 662 | 1.5 | 0.174 |
| 32 | 39.625 | 2.2726 | 318 | 6.1 | 343 | 0.8 | 0.087 |
| 33 | 40.351 | 2.2334 | 311 | 6.0 | 690 | 1.5 | 0.156 |
| 34 | 41.080 | 2.1954 | 288 | 5.5 | 1946 | 4.3 | 0.583 |
| 35 | 43.804 | 2.0650 | 372 | 7.1 | 1599 | 3.5 | 0.190 |

Its differential scanning calorimetry (DSC) shows one endothermic peak at 150±3° C. between 100-180° C.;

Its thermal gravimetric analysis (TG) shows that it does not contain crystal water or crystallization solvent;

It has a melting temperature between 146-151° C.

In another aspect, the present invention provides a method of preparing said Crystalline Form II of non-solvate of Apremilast, characterized in using a solvent that is a mixture of acetone and water, a mixture of THF and water or a mixture of acetone, THF and water, preferably a mixture of acetone and water. Specifically, said method comprising:

i) dissolving Apremilast or solvate thereof in acetone or THF at elevated temperature, then cooling to below 40° C.;

ii) slowly adding water in an amount of 0.5-2 times the volumes of acetone or THF under stirring, optionally seeding with Form II, and continue stirring for 30-180 min;

iii) adding water in an amount of 2-6 times the volumes of acetone or THF, stirring for 1-24 hr at 20° C. to refluxing temperature; and iv) filtering and drying to obtain Apremilast crystalline Form II.

Preferably, the above method comprises:

Dissolving Apremilast or solvate thereof in 2-10 times of acetone (ml/g) (preferably 3-5 times of acetone) at elevated temperature, then cooling to below 40° C.; slowly adding water in an amount of 0.5-2 times the volumes of acetone under stirring, optionally seeding with Form II, and continue stirring for 0.5-3 h at the same temperature; adding water in an amount of 2-6 times the volumes of acetone, stirring for 1-24 hr at 20° C. to refluxing temperature; filtering, flushing with water and drying to obtain Apremilast crystalline Form II as white solid. The X-ray powder diffraction patterns of the Form II are slightly different depend on the time of stirring after adding water, but the major characterizing peaks between 0-20 2θ remain the same (see FIGS. 2 and 5), the differential scanning calorimetry and thermal gravimetric analysis are substantially the same.

The inventors have surprisingly found that when crystallizing in acetone/water or THF/water, the crystallization temperature and the amount of water initially added have significant impact on the type of crystalline forms obtained.

A temperature under 40° C. is more favorable for the formation of Form II. More advantageously, seeding with Form II helps to accelerate the formation of Form II in the process of crystallization. After adding initial amount of water and stirring for 1-3 h, Crystalline Form II will precipitate; then add water in an amount of 2-6 times the volumes of acetone or THF, stir for 1-24 hr at 20° C. to refluxing temperature in order to obtain Form II fine powder; then cool, filter and dry to obtain Apremilast crystalline Form II.

In another aspect, the present invention provides a second method of preparing Apremilast Crystalline Form II, comprising suspending one or more of other crystalline forms of Apremilast with appropriate particle sizes (e.g., Forms A, B, C, D, E, F, G or Form I) in acetone/water mixture, THF/water mixture or THF/acetone/water mixture (preferably in acetone/water mixture), stirring for 1-72 h or even longer at 30° C. to refluxing temperature, then cooling, filtering and drying to obtain Crystalline Form II. Our study shows the smaller the particle size is, the time is shorter for being transformed into crystal form II. The less stable the crystal form is, it is easier to be transformed into crystal form II. The ratio of acetone to water is preferably 1:1-1:4.

In addition, crystallization in acetone/water can produce mixed crystals of Apremilast, i.e., mixed crystals comprising Apremilast Crystalline Form II and Apremilast Crystalline Form B; ratio of Form B to Form II in the mixed crystals can be adjusted by changing the ratio of acetone to water as well as the time and speed of adding water; in other words, the mixed crystals may comprise 0-100% of Form II. The X-ray powder diffraction patterns of the mixed crystals may vary significantly due to the different ratio of the two forms and the DSC pattern will show two absorption peaks at 150±3° C. and 157±3° C., respectively, the intensities of which may vary depend on the ratio of the two forms. In summary, whether Form II is present can be determined by the presence of the characterizing absorption peaks of Form II in the X-ray powder diffraction patterns, and can be further verified by presence of the absorption peak at 150±3° C. in DSC patterns.

Apparently, Apremilast mixed crystals can also be prepared by a method comprising: suspending other crystalline forms of Apremilast with appropriate particle sizes (e.g., Forms A, B, C, D, E, F or G) in acetone/water mixture, THF/water mixture or THF/acetone/water mixture, refluxing at 20° C. to refluxing temperature and stirring for different lengths of time; stirring time and temperature can be controlled to obtain mixed crystals with different ratio.

The Apremilast mixed crystals of the present invention comprise at least two crystalline forms, wherein at least one of the crystalline forms is Apremilast Crystalline Form II, and the other crystalline forms can be crystalline forms reported in prior art references, e.g., Forms A, B, C, D, E, F or crystalline form B or F are preferred.

Further, the Apremilast mixed crystals of the present invention are preferably consisted of Apremilast Crystalline Form II and Apremilast Crystalline Form B at any ratio. Obviously, mixed crystals of Crystalline Form II and Crystalline Form B can be used as active pharmaceutical ingredients. However, single Crystalline Form II is more preferred as active pharmaceutical ingredients in view of their thermodynamic stability.

Advantageously, crystallization in acetone/water can produce Apremilast Crystalline Form II as a white or off white product with high purity up to 99.8% and individual impurity less than 0.1%, and the optical isomerism of Apremilast substantially remains the same. However, Apremilast Crystalline Form B obtained by crystallizing in acetone or acetone/ethyl alcohol mixture is a light yellow product, and most unfavorably, the amount of R-isomer of the final product increases after each crystallization. CN102702070 reported a optical purity of 98% of the final product when intermediate having optical purity of 99.2% was used, and the product tends to agglomerate when drying; when large amount of ethyl alcohol was used, crystalline forms with large particle size will be produced, which are difficult to be crushed and are hard to be directly used in preparation processing.

More advantageously, the Apremilast Crystalline Form II of the present invention is obtained as powder; in some embodiments, particle size D90 is less than 15um. The product can be directly used in preparation processing without being crushed.

Specifically, Apremilast Crystalline Form II prepared in the present invention can be characterized by X-ray powder diffractometry (XRPD), infrared spectroscopy (IR) (KBr tabletting), differential scanning calorimetry (DSC), and thermal gravimetric analysis (TGA). Thermal gravimetric analysis (TGA) shows that there is no/substantially no solvate contained in the Crystalline Form II; its XRPD pattern is different from that of the Forms A, B, C, D, E, F, and G reported in Chinese patent CN102702070, thus it is a novel crystalline form. The test result is shown below.

The X-ray powder diffraction pattern shows the following significant characterizing absorption peaks at 2θ±0.2:

| #  | 2-Theta | d (A)  | Height | I%    | Area  | I%    | FWHM  |
|----|---------|--------|--------|-------|-------|-------|-------|
| 1  | 10.666  | 8.2876 | 568    | 10.9  | 1090  | 2.4   | 0.077 |
| 2  | 11.290  | 7.8312 | 3576   | 68.5  | 45434 | 100.0 | 0.234 |
| 3  | 12.573  | 7.0346 | 833    | 15.9  | 2789  | 6.1   | 0.111 |
| 4  | 13.203  | 6.7001 | 3140   | 60.1  | 31411 | 69.1  | 0.192 |
| 5  | 13.541  | 6.5338 | 2509   | 48.0  | 22813 | 50.2  | 0.174 |
| 6  | 13.874  | 6.3775 | 1946   | 37.3  | 17299 | 38.1  | 0.193 |
| 7  | 14.724  | 6.0114 | 5224   | 100.0 | 42800 | 94.2  | 0.149 |
| 8  | 16.223  | 5.4592 | 2582   | 49.4  | 21876 | 48.1  | 0.163 |
| 9  | 17.924  | 4.9448 | 2862   | 54.8  | 24450 | 53.8  | 0.164 |
| 10 | 18.751  | 4.7285 | 2068   | 39.6  | 15517 | 34.2  | 0.153 |
| 11 | 20.290  | 4.3731 | 1268   | 24.3  | 7487  | 16.5  | 0.139 |
| 12 | 20.725  | 4.2822 | 832    | 15.9  | 3836  | 8.4   | 0.143 |
| 13 | 21.531  | 4.1238 | 1573   | 30.1  | 8335  | 18.3  | 0.132 |
| 14 | 21.989  | 4.0388 | 1666   | 31.9  | 18358 | 40.4  | 0.277 |
| 15 | 22.778  | 3.9007 | 1887   | 36.1  | 19298 | 42.5  | 0.244 |
| 16 | 23.194  | 3.8317 | 1404   | 26.9  | 19738 | 43.4  | 0.375 |
| 17 | 25.265  | 3.5221 | 1412   | 27.0  | 22193 | 48.8  | 0.382 |
| 18 | 25.641  | 3.4714 | 1702   | 32.6  | 19926 | 43.9  | 0.268 |
| 19 | 26.587  | 3.3499 | 1904   | 36.4  | 20529 | 45.2  | 0.244 |
| 20 | 27.022  | 3.2970 | 3644   | 69.8  | 44458 | 97.9  | 0.234 |
| 21 | 27.596  | 3.2297 | 962    | 18.4  | 5166  | 11.4  | 0.194 |
| 22 | 28.226  | 3.1590 | 1147   | 22.0  | 7133  | 15.7  | 0.170 |
| 23 | 29.112  | 3.0648 | 581    | 11.1  | 973   | 2.1   | 0.103 |
| 24 | 29.667  | 3.0087 | 463    | 8.9   | 696   | 1.5   | 0.133 |
| 25 | 30.934  | 2.8884 | 482    | 9.2   | 1767  | 3.9   | 0.207 |
| 26 | 32.035  | 2.7916 | 486    | 9.3   | 1075  | 2.4   | 0.150 |
| 27 | 33.023  | 2.7103 | 450    | 8.6   | 1343  | 3.0   | 0.215 |
| 28 | 33.597  | 2.6653 | 473    | 9.1   | 2192  | 4.8   | 0.261 |
| 29 | 34.207  | 2.6191 | 509    | 9.7   | 2957  | 6.5   | 0.263 |
| 30 | 34.915  | 2.5676 | 404    | 7.7   | 1621  | 3.6   | 0.275 |
| 31 | 36.222  | 2.4779 | 336    | 6.4   | 662   | 1.5   | 0.174 |
| 32 | 39.625  | 2.2726 | 318    | 6.1   | 343   | 0.8   | 0.087 |
| 33 | 40.351  | 2.2334 | 311    | 6.0   | 690   | 1.5   | 0.156 |
| 34 | 41.080  | 2.1954 | 288    | 5.5   | 1946  | 4.3   | 0.583 |
| 35 | 43.804  | 2.0650 | 372    | 7.1   | 1599  | 3.5   | 0.190 |

The Apremilast crystalline Form II has an X-ray powder diffraction pattern comprising the following major characterizing absorption peaks at 11.2, 13.2, 13.5, 13.8, 14.7, 16.2, 17.9, 18.7, 20.2, 20.7, 27.0 2θ±0.2.

More importantly, the Apremilast crystalline Form II has an X-ray powder diffraction pattern comprising the following five characterizing absorption peaks at 11.2, 13.2, 13.5, 13.8, 14.7 2θ±0.2.

Lastly, the Apremilast Crystalline Form II has an X-ray powder diffraction pattern comprising the following two characterizing absorption peaks at 11.2, 14.7 2θ±0.2.

In another aspect, XRPD of Crystalline Form II produced in acetone and water may have different characterizing absorption peaks between 20-30° 2θ±0.2 due to measuring error, but the presence of Crystalline Form II can be determined in the obtained product by the major characterizing absorption peaks at a reflection angle of 2θ±0.2. More importantly, the characterizing absorption peaks between 10-20° at 2θ±0.2 are substantially the same (See FIGS. 2, 5, 6, 8, 12, 14, 16, and 17). There is no significant differences among the DSC patters, all of which show a single absorption peak at 150±3° C. between 100-180° C.

When compared with blank excipient, preparations comprising Apremilast Crystalline Form II as active pharmaceutical ingredient show the above major characterizing absorption peak, e.g., 11.2, 13.2, 13.5, 13.8, 14.7 etc, or 11.2, 14.7.

Apremilast Crystalline Form II has an DSC pattern comprising a single absorption peak at 150±3° C. between 100-180° C. Thermal gravimetric analysis (TG) pattern shows that there is no/substantially no crystallization solvents or water. Weight loss and decomposition was observed from about 250° C. (See FIG. 3). The melting temperature of Form II is 146-151° C.

Infrared spectroscopy (IR) shows that Form II has the following significant characterizing absorption peaks:
3002, 2932, 1763, 1697, 1621, 1519, 1480, 1428, 1394, 1367, 1340, 1297, 1269, 1234, 1163, 1139, 1095, 1044, 1028, 971, 908, 859, 826, 774, 750.

Below is a series of comparison studies among Form I, Form II and Form B.

1. Characterization of Form I, Form II and Form B: comparison of Apremilast Crystalline Form I, Form II and Form B is shown in Table 2.

TABLE 2

Comparison of Apremilast Crystalline Form I, Form II and Form B

| Form | Differential scanning calorimetry (DSC) | Thermal gravimetric analysis (TG) | XRPD | IR | melting temperatur |
|---|---|---|---|---|---|
| I | Two endothermic peaks 150 ± 3° C. and 157 ± 3° C. | Substantially no crystal water or solvent | Significantly different from Crystalline Form B | substantially the same | 154-157 |
| II | One endothermic peak 150 ± 3° C. | Substantially no crystal water or solvent | Totally different from Crystalline Form B | | 146-151 |
| B | One endothermic peak, 160 ± 3° C. | 0.24% | | | 154-160 |

2. Influence factors experiments of Form I, Form II and Form B:

In addition, the same batch of raw materials was crystallized in acetone/ethyl alcohol to produce Form B and crystallized in acetone/water to produce Form I and Form II, then compare the appearance and color of the products. Influence factors experiments of these three forms showed that Apremilast Crystalline Form I, Form II, and Form B were all stable under high temperature and high humidity conditions, both forms showed similar stability in light exposure experiments (see Table 3 below).

TABLE 3

Results of stability experiments of Form I, Form II and Form B

| Form | Color of the crystals | moisture absorption/ humidity 92.5% weight gain | Change of related substances | Change of related substances/light exposure for 10 days | Change of related substance/high temperature for 10 days |
|---|---|---|---|---|---|
| Form I | White or off white | <1.0% | essentially no change | essentially no change | Essentially no change |
| Form II | White or off white | <1.0% | | | |
| Form B | Off white or light yellow | <1.0% | | | |

3. Thermostability experiments of Form II and Form B:

Apremilast Crystalline Form II and Form B were suspended in water and stirred for 24-48 h under 60 and 100° C., respectively, then cooled, filtered, and dried, and X-ray powder diffraction patterns, DSC patterns, melting temperature and related substance were determined (see Table 4).

TABLE 4

Thermostability experiments of Form II and Form B

| | 60° C., 48 h | | | 100° C., 24~48 h | | |
|---|---|---|---|---|---|---|
| Form | X-ray powder diffraction | DSC | melting temperature | X-ray powder diffraction pattern | DSC | melting temperatur |
| Form II | essentially no change | 150° C. | essentially no change | essentially no change | 150° C. | essentially no change |
| Form B | weak absorption peak at 14.7 | 157° C. | Decreased 2-3° C. | Weak absorption peaks at 11.2 and 14.7, correspond to the positions of the strong absorption peaks | 150° C. 157° C. | Decreased 3-4° C. |

The above experimental results showed that Apremilast Crystalline Form B is less thermodynamically stable than Apremilast Crystalline Form II; the X-ray powder diffraction pattern and DSC pattern of heated Form B shows charactering absorption peaks of Form II, and the patters of Form II did not show any substantial change. More advantageously, under the same micronization condition, Form II showed weak or no electrostatic effect, while Form B showed higher electrostatic effect. In addition, when Form B was suspended in water at 100° C. and stirred for 24 h, filtered and dried, serious electrostatic effect was observed, while Form II showed essentially no electrostatic effect. Large electrostatic effect will adversely affect the preparation processing. When stirred at 100° C. for 48 h, both forms showed no significant change in optical isomerism; the amount of related substance, N-deacetylates, increased, wherein the increased amount of Form B is slightly larger than that of Form II (i.e., 0.059% and 0.046%, respectively), the difference was not significant.

4. Conversion of Forms A, B, C, D, E, F, G to Form II

In addition, pure Form II can obtained by suspending crashed Forms A, B, C, D, E, F and/or G in acetone/water and stirring at 50° C. to refluxing temperature for 1-48 h. This again shows that Form II is more thermodynamically stable than Form B.

Amongst Forms A, B, C, D, E, F, and G reported by Celgene, Form B are considered to be the most thermodynamically stable form and thus suitable for medicinal use. Our experiments show that Form II is even more stable than Form B, thus is more suitable for long term storage and can be used as medicinal Crystalline in preparation processing.

5. Solubility experiments of Form B and Form II

The solubility of Form II and Form B in common solvents such as acetone, butanone, ethyl alcohol, methanol, ethyl acetate, acetonitrile, dichloromethane, tetrahydrofuran, petroleum ether, n-hexane, water was tested and compared. The experiment results shows that there is essentially no difference between Form II and Form B.

6. Pharmacokinetic study of Form B and Form II in animal

1) In vivo absorption tests on rats

Pharmacokinetic study of Apremilast Crystalline Form B and Form II with similar particle sizes in SD rats showed that both Apremilast Crystalline Form II of the present invention and Apremilast Crystalline Form B showed significant sexual difference; both forms showed similar $T_{max}$, $C_{max}$, $T_{1/2}$. In female rats, the exposure of Form II was 1.5 times of the exposure of Form B, thus Form II has stronger in vivo activity.

7. Pharmaceutical compositions

As one aspect of the present invention, the present invention also provides a pharmaceutical compositions comprising said Crystalline Form II of the non-solvate of Apremilast as active pharmaceutical ingredient and a pharmaceutically acceptable carrier, wherein the active pharmaceutical ingredient comprises 1-100% of Apremilast Crystalline Form II.

Obviously, similar to the uses and indications of Form B, Crystalline Form II of the non-solvate of Apremilast prepared according to the present invention can be used to treat disease or disorder that can be ameliorated by the inhibition of TNF-α, wherein the disease or disorder is selected from psoriasis, psoriatic arthritis, ankylosing spondylitis, rheumatoid arthritis, atopic dermatitis, dental ulcer in patients having behcet disease, chronic skin sarcoid, giant cell arteritis, Parkinson's disease, prurigo nodularis, lichen planus, complex oral disorder, lupus, hepatitis, uveitis, sicca syndrome, depression, interstitial cystitis, vulvodynia, prostatitis, osteoarthritis, diffuse large B cell lymphoma, polymyositis, dermatomyositis, inclusion body myositis, erosive osteoarthritis, endometriosis, radicular neuropathy, and gangrenous pyoderma or chronic obstructive pulmonary disease.

In another aspect, Crystalline Form II of the non-solvate of Apremilast prepared according to the present invention can be used to treat disease or disorder that can be ameliorated by the inhibition of PDE4, wherein the disease or disorder is selected from HIV, hepatitis, adult respiratory distress syndrome, bone resorption disease, chronic obstructive pulmonary disease, chronic inflammatory lung diseases, dermatitis, inflammatory skin disease, atopic dermatitis, cystic fibrosis, septic shock, sepsis, endotoxic shock hemodynamic shock, sepsis syndrome, post ischemia reperfusion injury, meningitis, psoriasis, fibrosis disease, psoriatic arthritis, cachexia, transplant rejection, graft-versus-host disease, autoimmune disease, rheumatoid spondylitis, arthritis, ankylosing spondylitis, rheumatoid arthritis, osteoarthritis, osteoporosis, segmental enteritis, ulcerative colitis, inflammatory bowel disease, multiple sclerosis, systemic lupus erythematosus, erythema nodosum leprosum in lepriasis, radiation damage and hyperoxic lung injury.

In addition, Crystalline Form II of the non-solvate of Apremilast prepared according to the present invention can be used to treat cancer, wherein the cancer is selected from multiple myeloma, malignant melanoma, spongioblastoma, leukemia and solid tumor.

Lastly, Crystalline Form II of the non-solvate of Apremilast prepared according to the present invention can be used to treat sarcoidosis, wherein the sarcoidosis is selected from cardiac sarcoidosis, cutaneous sarcoidosis, hepatic sarcoidosis, oral sarcoidosis, nervous system sarcoidosis, nasal sinus sarcoidosis, Ralph Glenn syndrome, frostbite lupus, uveitis, or chronic cutaneous sarcoidosis.

Obviously, Crystalline Form II of the non-solvate of Apremilast can be used as active pharmaceutical ingredient for treating the above mentioned diseases and disorders. Appropriate dosage forms include tablets, capsules, dispersible tablets, orally disintegrating tablets, etc; excipients can be selected from, but are not limited to, lactose, mannitol, polyvinylpolypyrrolidone, aerosil, magnesium stearate, microcrystalline cellulose, sodium carboxymethylcellulose, hydroxy propyl cellulose, croscamiellose sodium, preferably selected from lactose, microcrystalline cellulose, croscarmellose sodium, aerosil, and magnesium stearate.

Apremilast mentioned in the present invention can be easily prepared according to the methods described in prior art references such as U.S. Pat. No. 6,020,358, U.S. Pat. No. 6,962,940 or CN201410335852.6.

BRIEF DESCRIPTION OF THE FIGURES

The figures included in the present application constitute parts of the specification, and can be used to illustrate the present invention together with the specification and claims.

DEVICES AND TESTING METHODS

Figure 1:
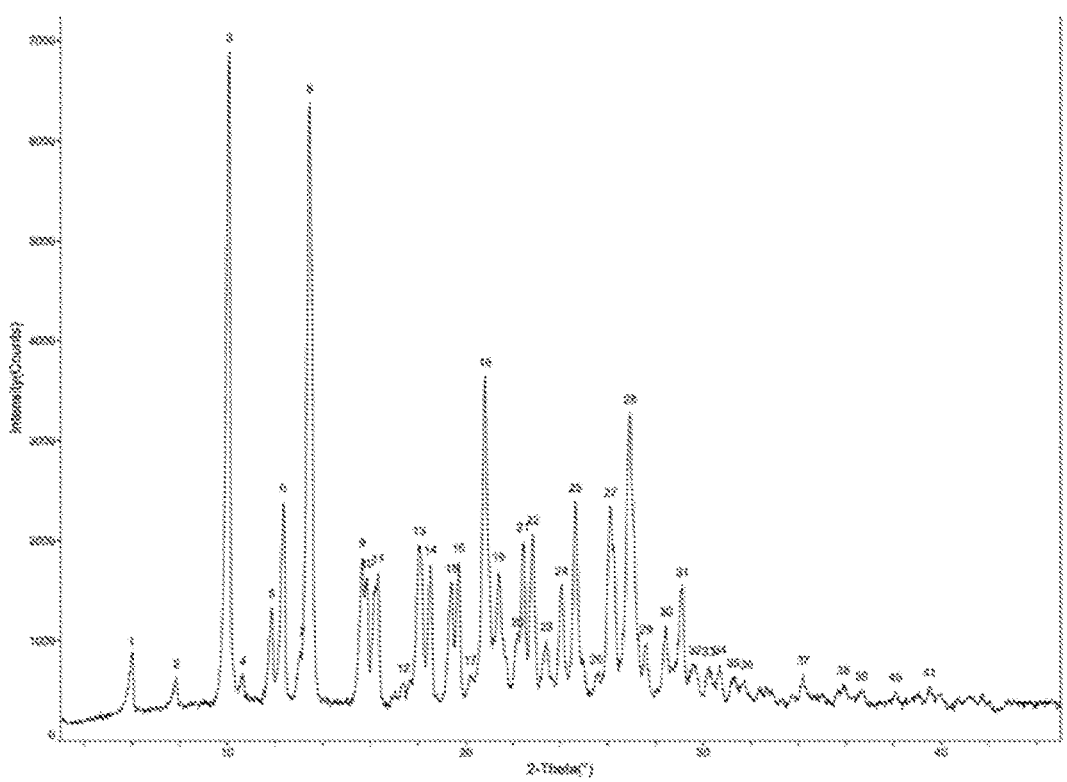
FIG. 1: XRPD pattern of Form B.
Figure 2:
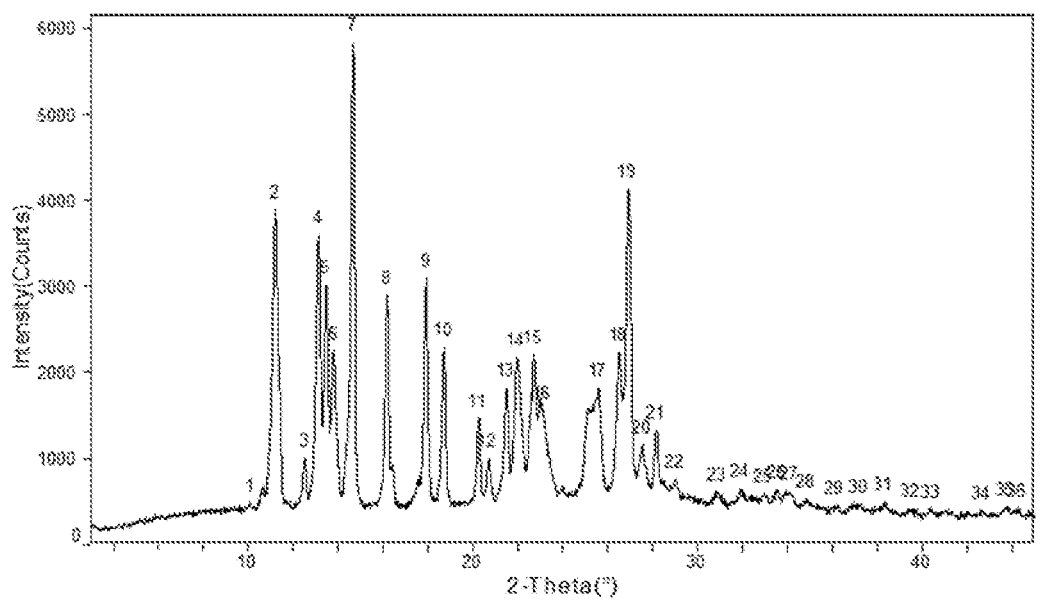
FIG. 2: XRPD pattern of Form II (stirring for 4 hs after adding water)
Figure 3:
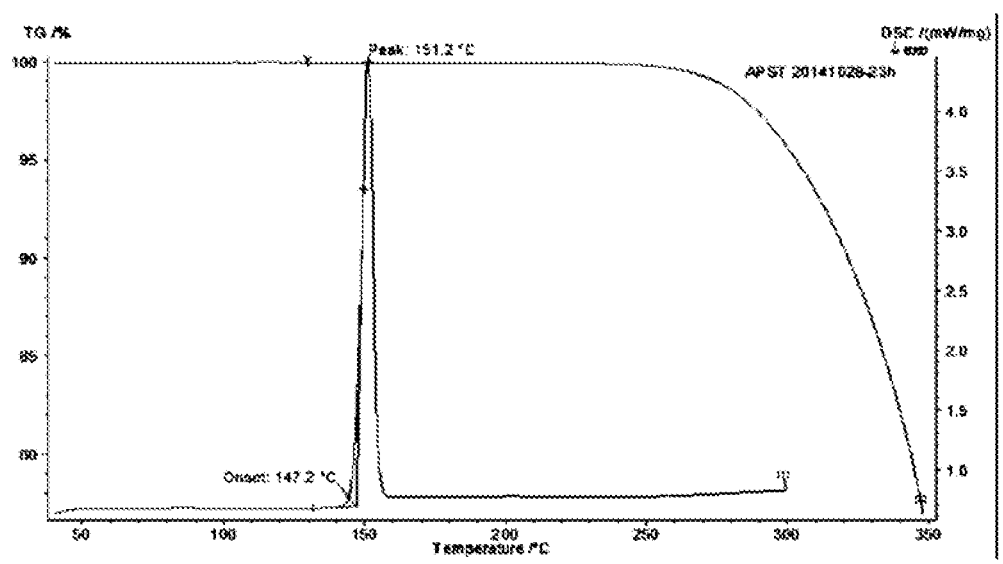
FIG. 3: TG pattern and DSC pattern of Form II (stirring for 23 hs after adding water)
Figure 4:
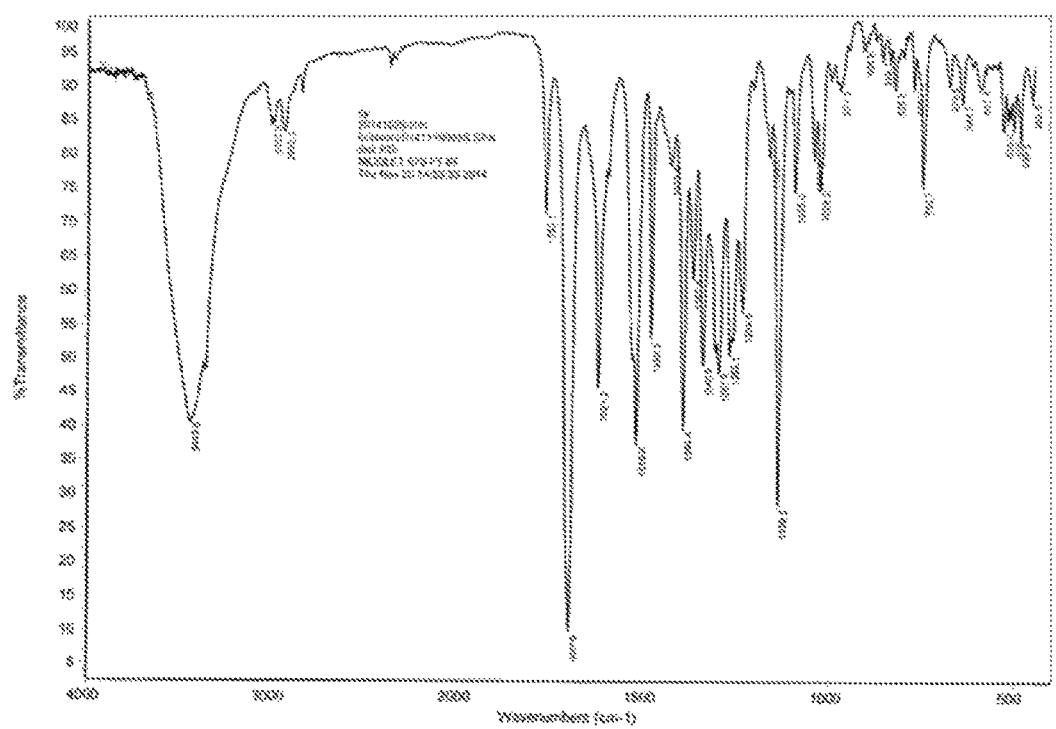
FIG. 4: IR pattern of Form II (stirring for 23 hs after adding water)
Figure 5:
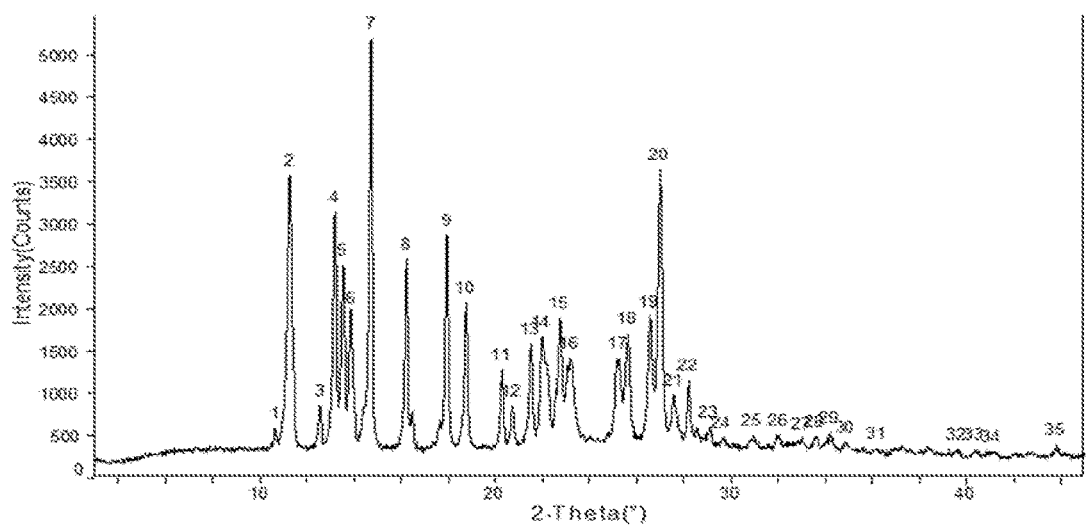
FIG. 5: XRPD pattern of Form II (stirring for 23 hs after adding water)
Figure 6:
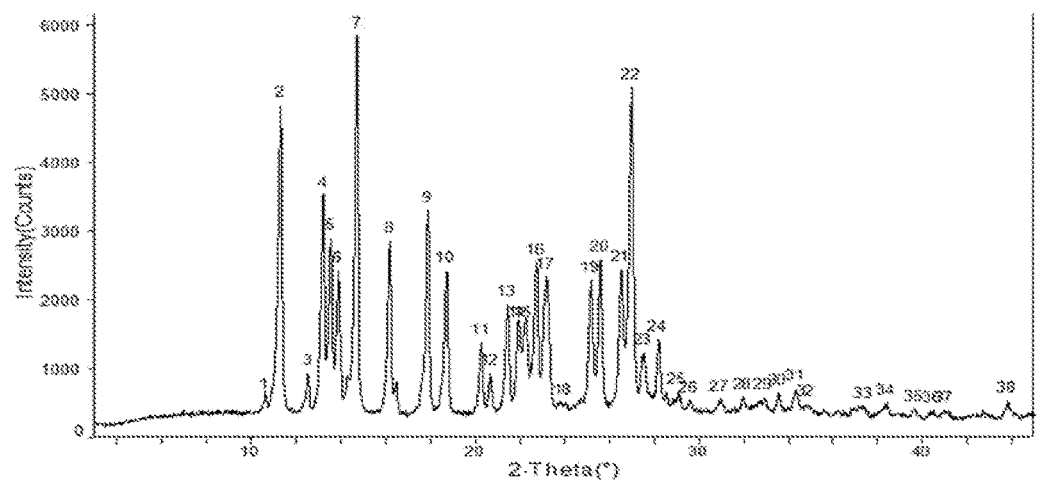
FIG. 6: XRPD pattern of Form II (stirring for 48 hs at 60° C.)
Figure 7:
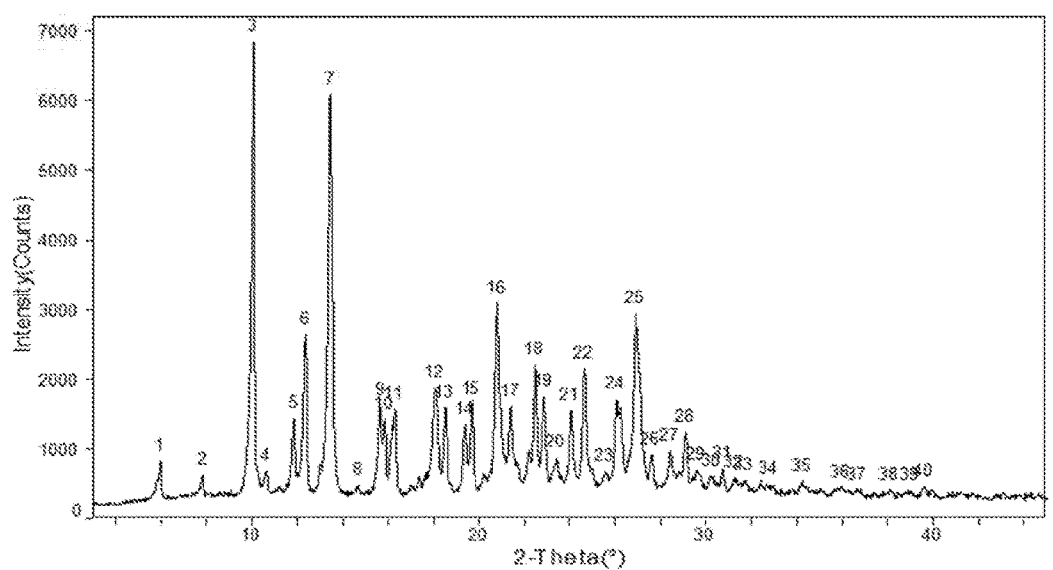
FIG. 7: XRPD pattern of Form B (stirring for 48 hs at 60° C.)
Figure 8:
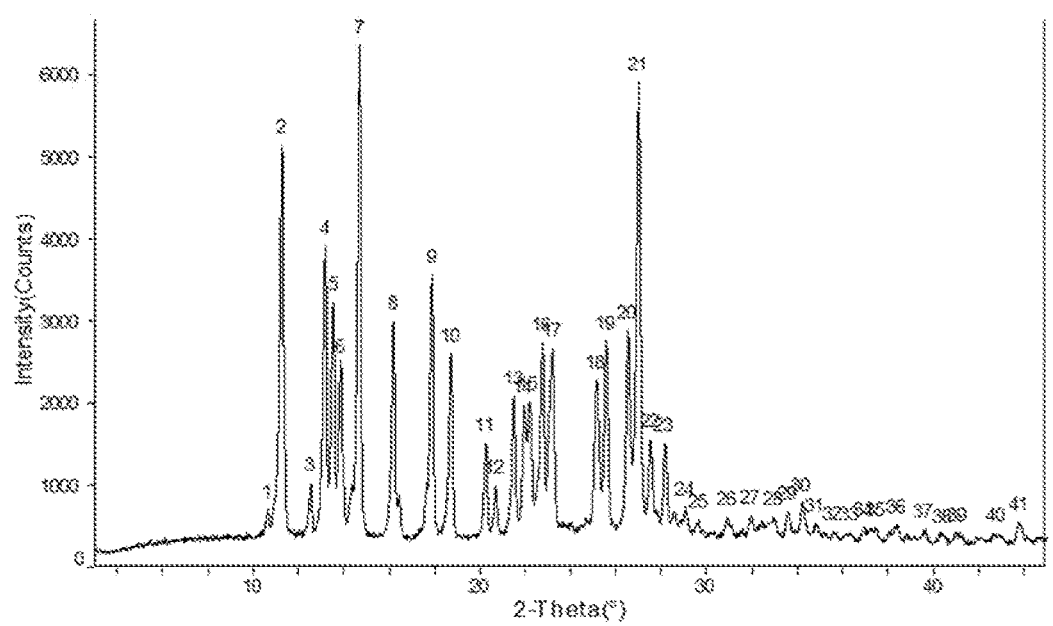
FIG. 8: XRPD pattern of Form II (stirring for 24 hs at 100° C.)
Figure 9:
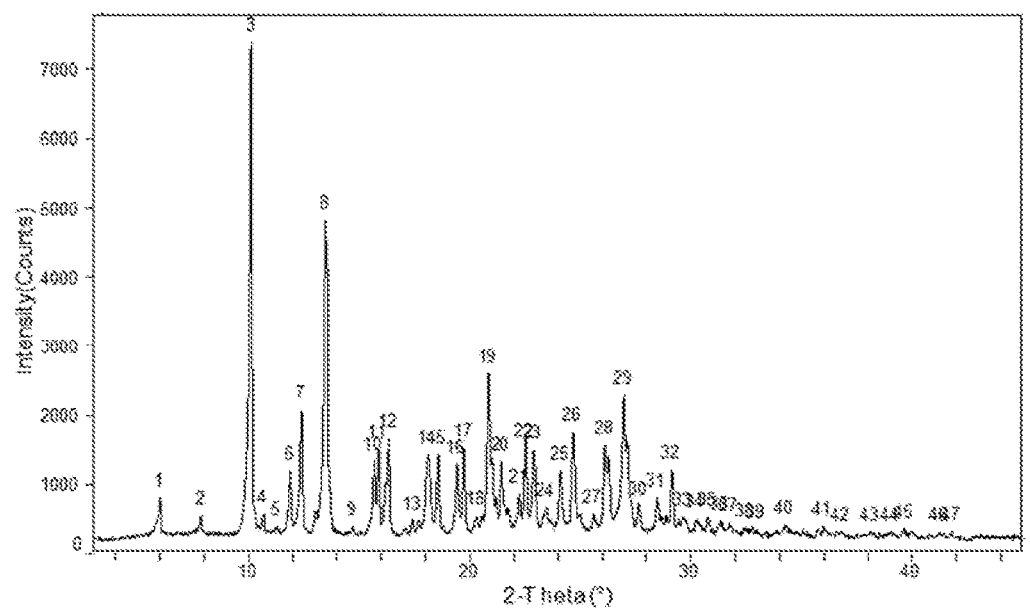
FIG. 9: XRPD pattern of Form B (stirring for 24 hs at 100° C.)
Figure 10:
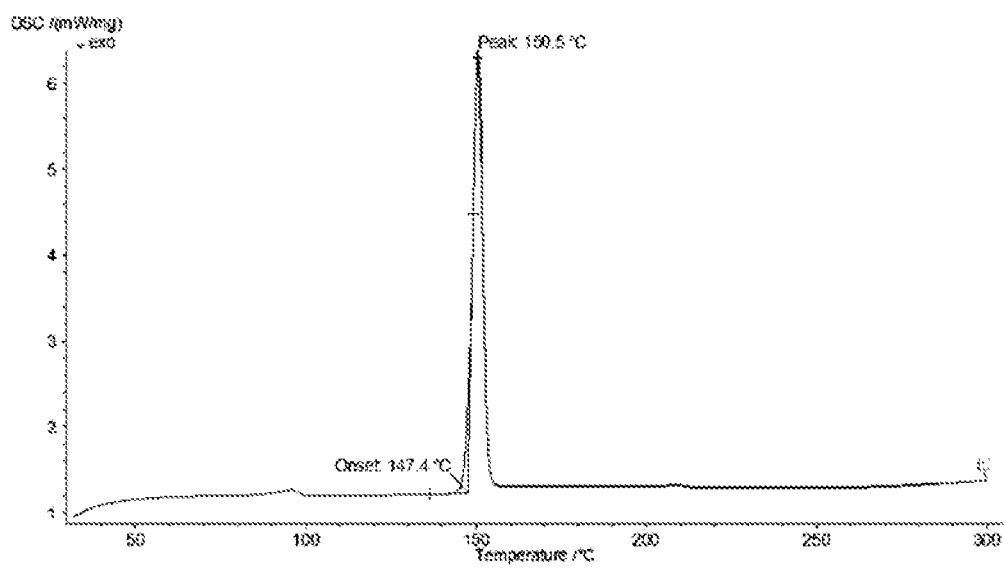
FIG. 10: DSC pattern of Form II (stirring for 24 hs at 100° C.)
Figure 11:
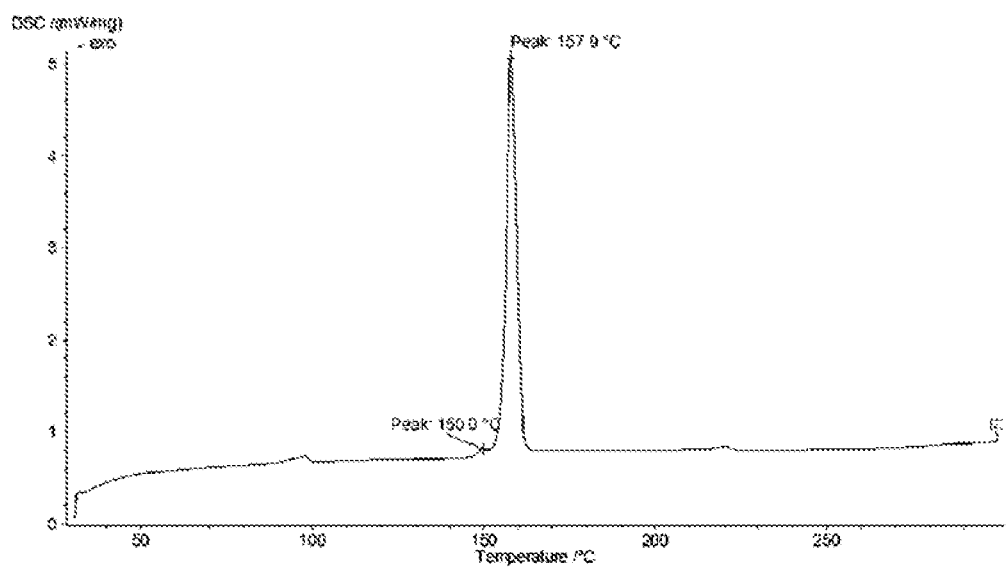
FIG. 11: DSC pattern of Form B (stirring for 24 hs at 100° C.)
Figure 12:
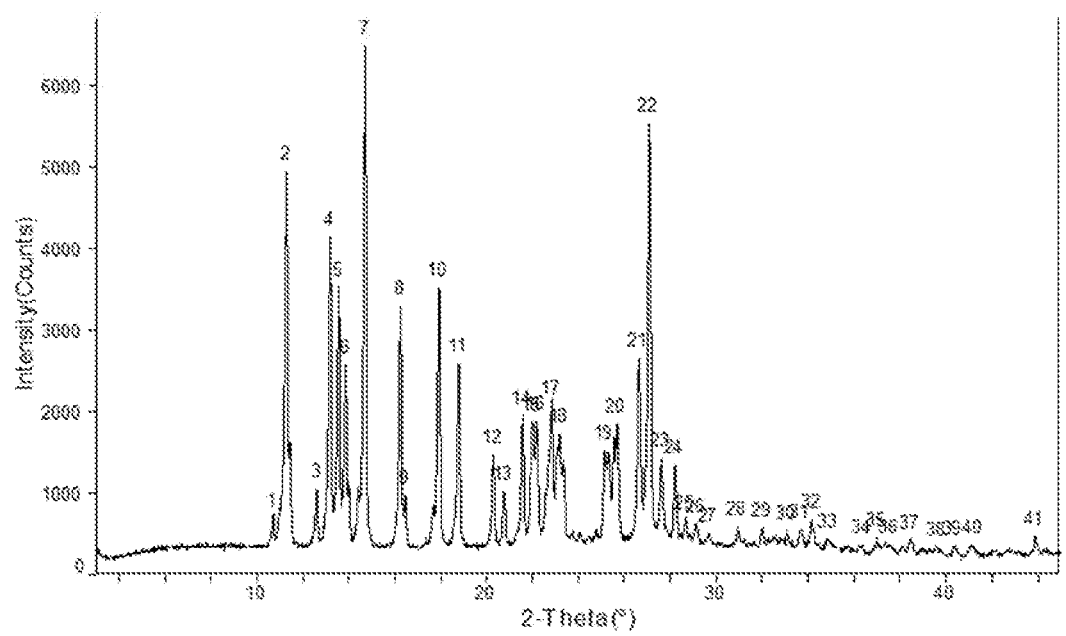
FIG. 12: XRPD pattern of the product obtained by suspending Form B in acetone/water and stirring for 36 hs at 70° C.
Figure 13:
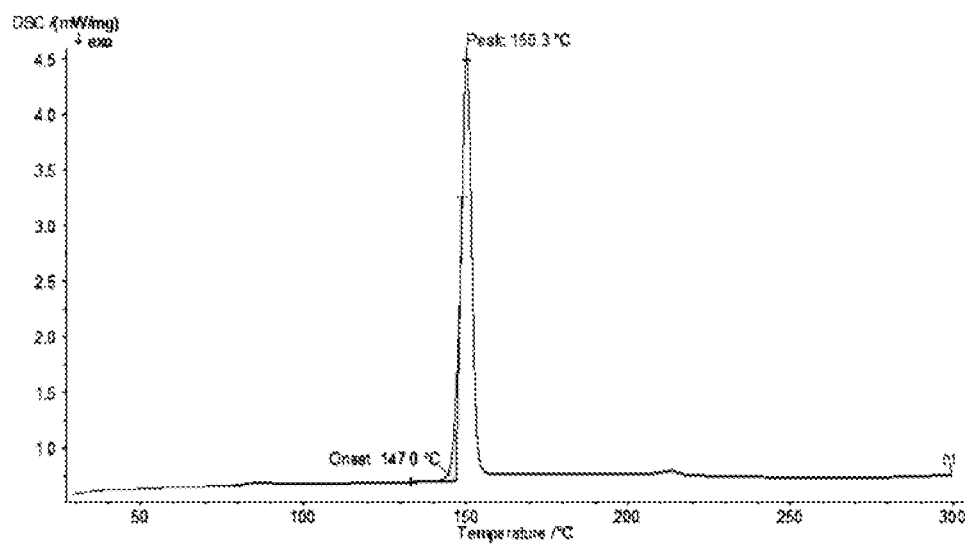
FIG. 13: DSC pattern of the product obtained by suspending Form B in acetone/water and stirring for 36 h at 70° C.
Figure 14:
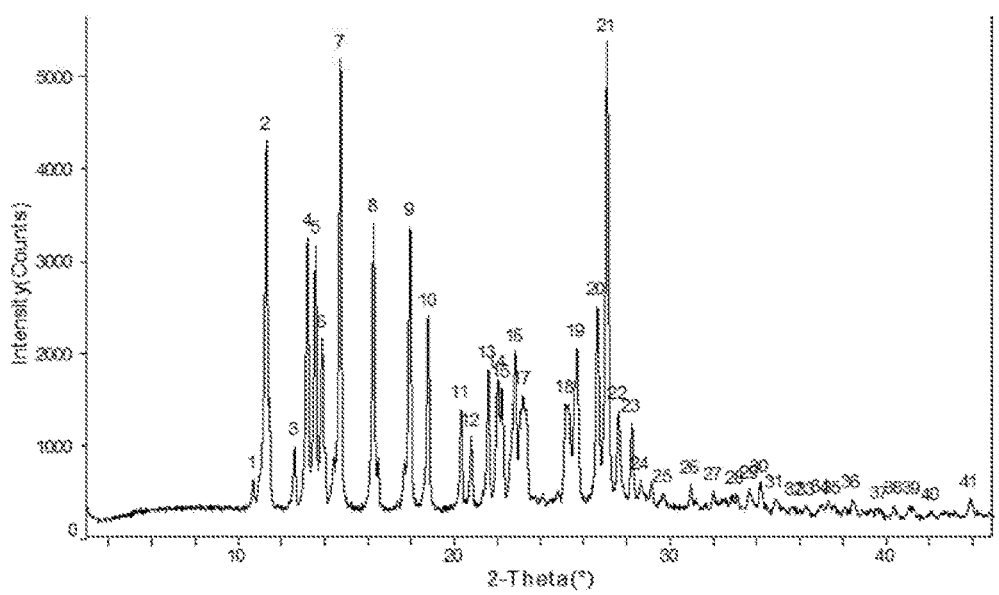
FIG. 14: XRPD pattern of the product obtained by suspending Form D in acetone/water and stirring for l0 h at 70° C.
Figure 15:
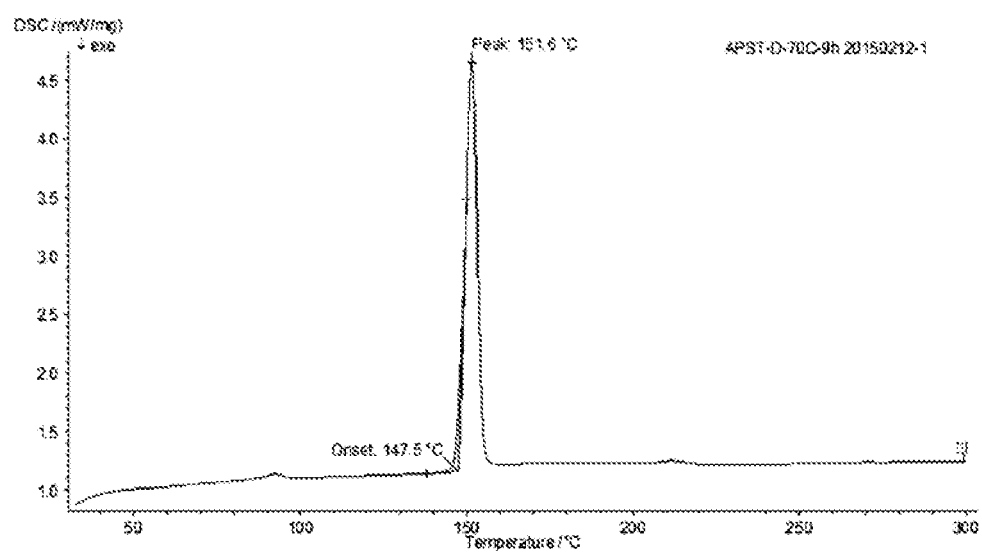
FIG. 15: DSC pattern of the product obtained by suspending Form D in acetone/water and stirring for 10 h at 70° C.
Figure 16:
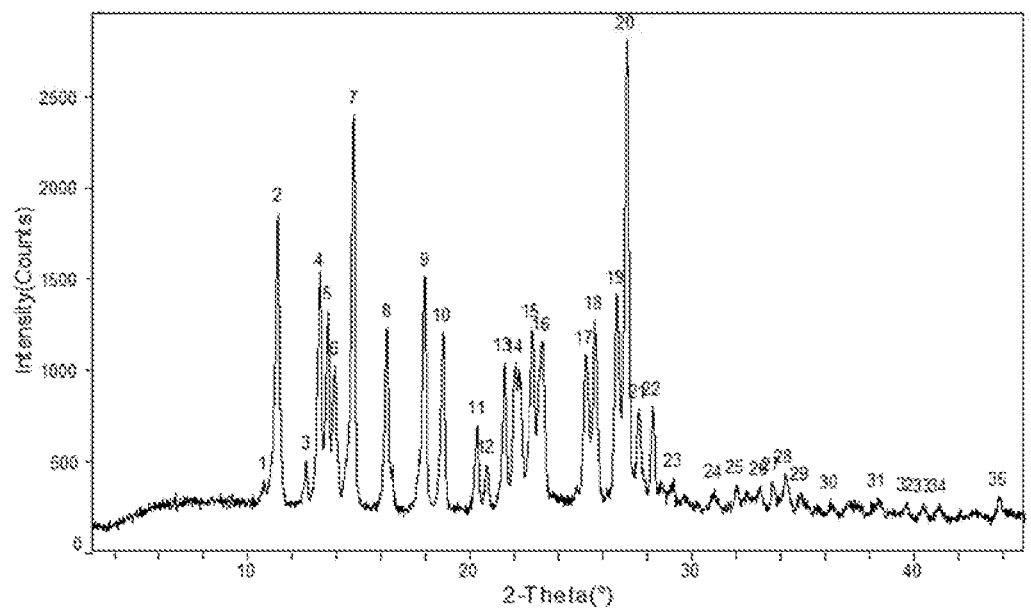
FIG. 16: XRPD pattern of Form II.
Figure 17:
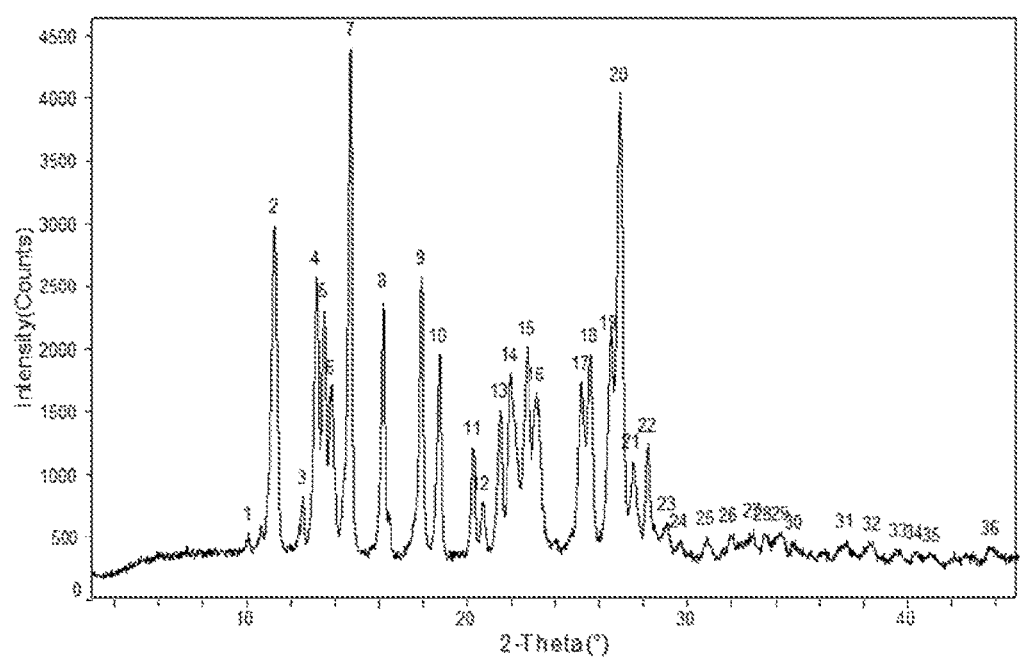
FIG. 17: XRPD pattern of Form II.
Figure 18:
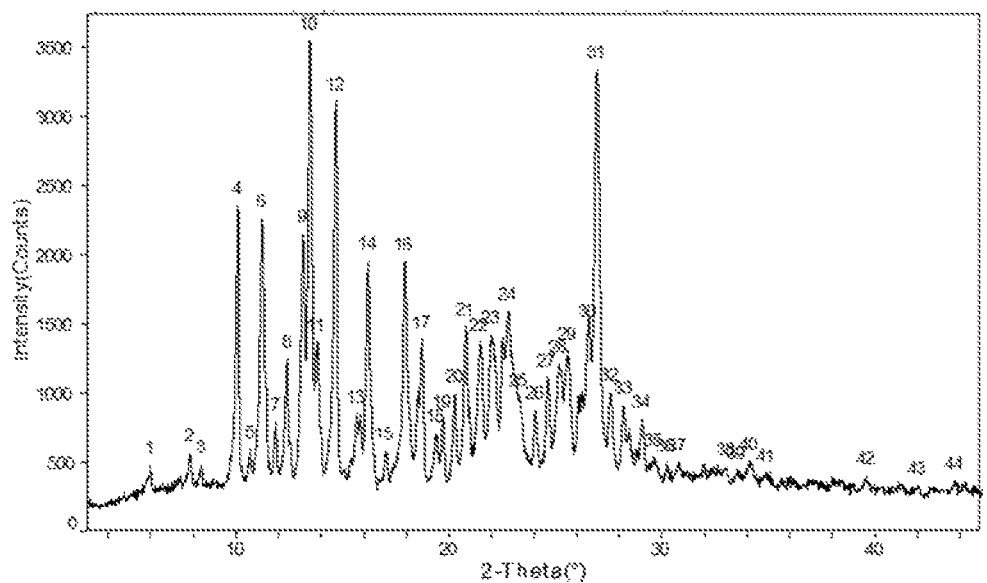
FIG. 18: XRPD pattern of mixture of Form II and Form B (The ratio is roughly 1:1)
Figure 19:
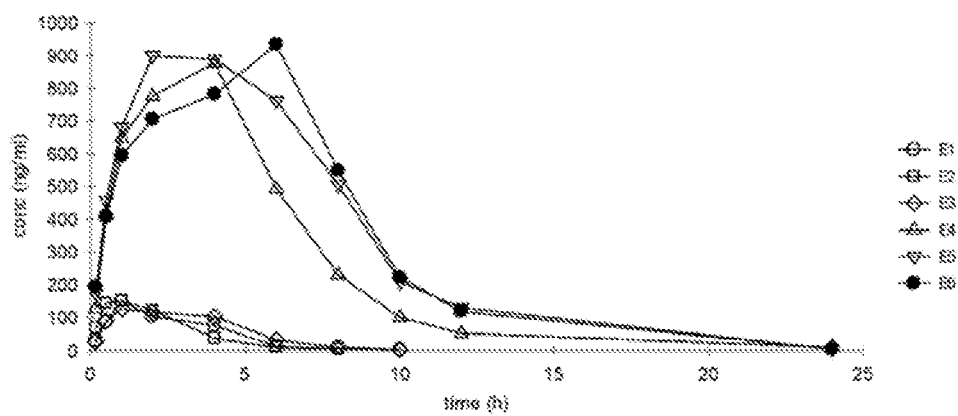
FIG. 19: Plasma concentration vs. time plot of rats gavaged with 10 mg/kg APST-B.
Figure 20:
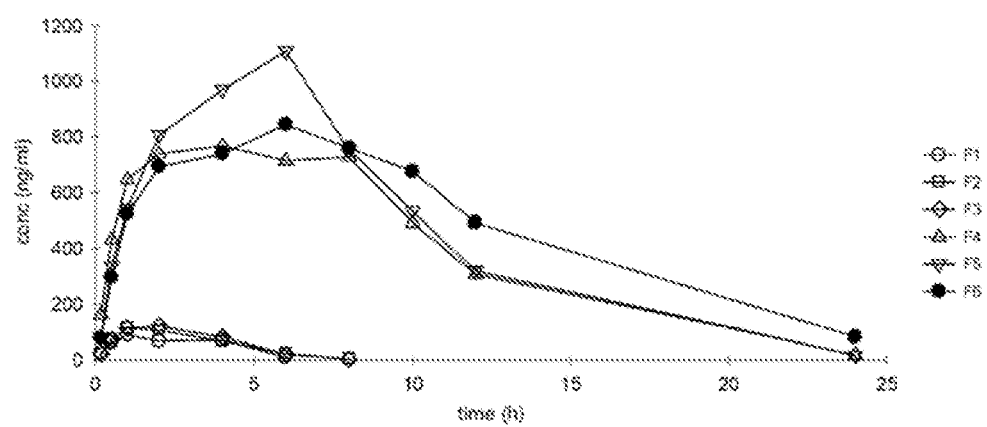
FIG. 20: Plasma concentration vs. time plot of rats gavaged with 10 mg/kg APST-II.
Figure 21:
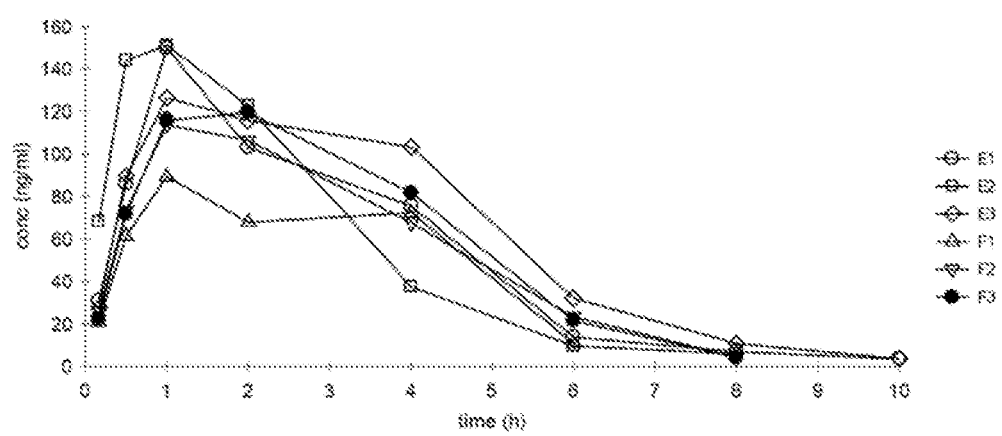
FIG. 21: Plasma concentration vs. time plots of male rats gavaged with 10 mg/kg APST-B and APST-II, respectively.
Figure 22:
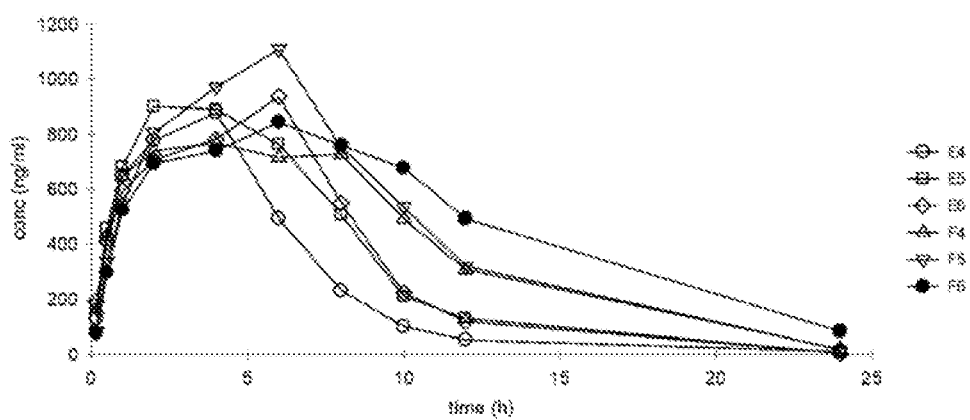
FIG. 22: Plasma concentration vs. time plots of female rats gavaged with 10 mg/kg APST-B and APST-II, respectively.

1. X-ray powder diffraction pattern (XRPD):
Device model: Bruker D8 ADVANCE, X-ray powder diffractometer
Experiment conditions: optical source: CuKα 40Kv 40mA; divergence slit: 1mm; soller slit: 0.4mm; scan mode: continuous scan; scanned area: 3°~45'; sampling interval: 0.02° ; scan speed: 8° /min.
2. Infrared spectroscopy
Device model: NICOLET 670-FTIR
Experiment condition: KBr tabletting
3. DSC parmeters:
Device model: NETZSCH DSC 204 F1
Crucible type: alumina crucible (Needle punched)
Sweep gas: high purity nitrogen, 20 mL/min
Shielding gas: high purity nitrogen, 60 mL/min
Temperature increase rate: 10° C./min
4. TG parmeters
Device model: NETZSCH TG 209 F1
Crucible type: aluminium oxide crucible
Sweep gas: high purity nitrogen, 20 mL/min
Shielding gas: high purity nitrogen, l0 mL/min
Temperature increase rate: 10° C/min
5. melting temperature:
RD-1 melting temperature tester, Tianjin Xuyang Scientific Instruments Equipment Co., Ltd.
6. Particle size detection:
Mastersizer 2000 particle size tester, Malvern Instruments Ltd.

DETAILED DESCRIPTION

The present invention will be further illustrated by the Examples below. However, the Examples shall not be construed as any limitations on the present invention. Any modification of temperature or ratio of solvents falls into the protection scope of the present patent.

EXAMPLE 1

Apremilast Crystalline Form II

Apremilast (10.0 g) and acetone 35ml were added to a three-necked flask and were heated to dissolve, then cooled to below 35° C. 0.5-3.0 volumes of purified water was slowly added, small amount of Form II was added as seed crystal, stirred for 1 h until the product precipitated, then 2 times of purified water by volume (70 ml) was added, stirred at 15-20° C. overnight (totally about 24 h), filtered and rinsed with water, dried at 60° C. to provide about 9.32 g of Apremilast Crystalline Form II, mp:147.2-149.8° C.

EXAMPLE 2

Apremilast Crystalline Form II

Apremilast (400.0 g) and acetone 1200ml were added to a three-necked flask and were heated to dissolve. 0.5-3.0 volumes of purified water was slowly added, small amount of Form II was added as seed crystal, stirred for 1 h until the product precipitated, then 2 times of purified water by volume (2.4L) was added, stirred at 10-60° C. overnight (totally about 18 h), filtered and rinsed with water, dried at 60° C. to provide about 392.3 g of Apremilast Crystalline Form II, mp: 147.2-150.2° C.

EXAMPLE 3

Apremilast Crystalline Form B

Apremilast (10.0 g) and acetone (30 ml) were added to a three-necked flask and were heated to dissolve, then cooled to below 30° C. 10 ml of purified water was slowly added, cooled and stirred until the product precipitated, stirred for 2 h, then water (100 ml) was slowly added, kept warm and stirred overnight (about 24 h), filtered and rinsed with water, dried at 60° C. to obtain about 9.45 g of Apremilast Crystalline Form B, mp: 156.2-157.8° C.

EXAMPLE 4

| | |
|---|---|
| Apremilast Crystalline Form II | 30.0 g |
| lactose | 200.0 g |
| microcrystalline cellulose | 60.0 g |
| croscarmellose sodium | 10.0 g |
| aerosil | 4.0 g |
| magnesium stearate | 2.0 g |

The main drag was passed through a 200 mesh screen, the filler and disintegrating agent were passed through a 80 mesh screen; prescribed amounts of filler and disintegrating agent were weighted and mixed, then the mixture and the main drug were mixed by method of increment by equal quantity, then prescribed amounts of glidant and lubricant were added, mixed uniformity then tabletting.

EXAMPLE 5

| | |
|---|---|
| Apremilast Crystalline Form II | 15.0 g |
| Lactose | 60.0 g |
| micro crystalline cellulose | 62.0 g |
| croscarmellose sodium | 8.0 g |
| aerosil | 2.0 g |
| magnesium stearate | 1.0 g |

The main drug was passed through passed through a 200 mesh screen, the filler and disintegrating agent were passed through a 80 mesh screen; prescribed amounts of filler and disintegrating agent were weighted and mixed, then the mixture and the main drug were mixed by method of increment by equal quantity, then prescribed amounts of glidant and lubricant were added, mixed uniformity then tabletting.

EXAMPLE 6

Thermodynamical Stability Studies of Form II and Form B

Apremilast Crystalline Form II and Form B were suspended in water, respectively, stirred at 60-100° C. for 48 h sampled at a certain time interval and filtered, dried to determine the change of melting temperature; sampled at 24 h, 48 h, filtered and dried to determine change of XRPD patterns, DSC patterns, melting temperature, electrostatic effects, and related substances.

EXAMPLE 7

Apremilast Crystalline Form B Conversion Study

Apremilast Crystalline Form B (5.0 g, particle size less than 300 mesh) was suspended in 60 ml acetone/water (1:3), heated to refluxing temperature and stirred for 36 h, then cooled while stirring, filtered, dried at 60° C. to obtain about 4.88 g of Apremilast Crystalline Form II, mp:148.3-150.3° C.

XRPD pattern and DSC pattern demonstrated complete conversion to Form II.

EXAMPLE 8

Apremilast Crystalline Form D Conversion Study

Apremilast Crystalline Form D (5.0 g, particle size less than 200mesh) was suspended in 60ml acetone/water (1:3), heated to refluxing temperature and stirred for 8-10 h, then cooled while stirring, filtered, dried at 60° C. to obtain about 4.60 g of Apremilast Crystalline Form II, mp:148.3-150.5° C.

XRPD pattern and DSC pattern demonstrated complete conversion to Form II.

EXAMPLE 9 in vivo Pharmacokinetic Comparison Study of Apremilast Crystalline Form B and Form II in SD Rats 1. Control of Particle Sizes of the Crystals The particle sizes of the two forms are controlled by micronization (see below):

| | D 0.1 | D 0.5 | D 0.9 |
|---|---|---|---|
| Apremilast Crystalline Form B (APST-B) | 1.052 um | 6.792 um | 55.073 um |
| Apremilast Crystalline Form II (APST-II) | 1.395 um | 8.722 um | 58.942 um |

2. Method:

Twelve SD rats weight 200-220 g with half males and half females were divided randomly into 2 groups (named as group A and group B).

| | Animal No. | | | |
|---|---|---|---|---|
| | E1~3 | E4~6 | F1~3 | F4~6 |
| Gender | ♂ | ♀ | ♂ | ♀ |
| Form | APST-B | | APST-II | |

According to the administration route and dosage amounts provided in FDA references, the two crystalline forms were given by gavage to investigate their pharmacokinetic behaviors in rats. The dosage amounts of the two forms are both 10 mg/kg (solvent is 1% carboxymethylcellulose). The rats were fasted for 12 hs before the study, food was provided 4 hs after administration, water deprivation was not required during the whole study.

Blood was collected via the fundus venous plexus 10, 30mins, 1, 2, 4, 6, 8, 10, 12 and 24 hs after administration. The collected blood was placed on ice and centrifuged for 5min at 8000 rpm, plasma was separated, and cryoperserved in a −20° C. refrigerator. LC-MS/MS was used to determine the concentration of APST in plasma. Linearity range of APST in plasma is 2-1000ng/ml, the linearity was good.

3. Experimental Results

Plasma concentration vs. time plots of rats gavaged with 10 mg/kg APST-B and APST-II suspensions, respectively, were shown in FIGS. 19-22.

4. Result Analysis

The major pharmacokinetic parameters of APST in rats gavaged with 10 mg/kg APST-B and APST-II suspensions, respectively; are shown below: time to peak $T_{max}$ were 1.6 h (median 2.5 hs) and 1-6 h (median 3 hs); peak concentrations $C_{max}$ were, respectively, 523.05±417.46 and 506.90±451.89 ng/ml, plasma concentration vs. time plots area under the curve $AUC_{0-t}$ were, respectively, 3766.48±3617.82 and 5533.11±5613.02 ng·h/ml, the exposure of 10 mg/kg APST-B in rats was about 68.07% of the exposure of APST-II, the difference between the two groups was quite large, and the difference of exposure between females and males were very large, the difference of the exposure between the two groups was not statistically significant due to the large standard deviation. Thus, the pharmacokinetics in females and males were analyzed separately below.

The major pharmacokinetic parameters of APST in male rats gavaged with 10 mg/kg APST-B and APST-II suspensions, respectively, are shown below: time to peak $T_{max}$ were 1 h (median 1 h) and 1-2 h (median 1 h); peak concentrations $C_{max}$ were, respectively, 142.4±13.96 and 107.63±16.05 ng/ml, plasma concentration vs. time plots area under the curve $AUC_{0-t}$ were, respectively, 530.44±70.05 and 445.59±81.25 ng·h/ml, the $C_{max}$ and $AUC_{0-t}$ of 10 mg/kg APST-B in male rats were about 132.3% and 119.0%, respectively, of those of APST-II; the results showed that the absorption of APST-B in male rats was better than APST-II, but the difference was not statistically significant.

The major pharmacokinetic parameters of APST in female rats gavaged with 10 mg/kg APST-B and APST-II suspensions, respectively, are shown below: time to peak $T_{max}$ were 2-6 h (median 4 h) and 4-6 h (median 6 h); peak concentrations $C_{max}$ were, respectively, 903.7±28.47 and 906.17±178.89ng/ml, plasma concentration vs. time plots area under the curve $AUC_{0-t}$ were, respectively, 7002.52±1140.54 and 10620.62±1053.56 ng·h/ml, the $AUC_{0-t}$ of 10 mg/kg APST-B in female rats was 65.9% of that of APST-II; the results showed that the absorption of APST-B in female was lower than APST-II, and the difference was statistically significant (P<0.05).

EXAMPLE 10

Study on Comparison of Pharmacokinetics Study of Apremilast Crystal Form B and Apremilast Crystal Form II in Beagle Dogs 1. Particle size control of crystal form
Same as example 9.

2. Method 6 healthy Beagle dogs weight 6-8 kg with half males and half females were divided randomly into 2 groups, each group having 3.

According to the administration route and dosage amounts, medicine is administrated orally and the dosage is 30 mg/dog/time. After crude drug powder of two crystal forms being weighed about 30 mg respectively, capsule shell is used to be filled and 10 ml water is used accompanied with administration. The Beagle dogs were fasted for 12 hours before the study, and food is provided in 4 hours after administration. Water deprivation was not required during the whole study. Specific administration groups are designed in the table as below.

| | | Animal number | | | | | |
|---|---|---|---|---|---|---|---|
| | | 1 | 2 | 3 | 4 | 5 | 6 |
| | | | | Gender | | | |
| | | ♂ | ♀ | ♂ | ♀ | ♂ | ♀ |
| | | | | Animal group | | | |
| | | | A | | | B | |
| First Cycle | Dog number | 1-1 | 1-2 | 1-3 | 1-4 | 1-5 | 1-6 |
| | Capsule | | APST-B | | | APST-II | |

0.5ml venous blood was collected via the small saphenous veins 10, 30 min, 1, 2, 4, 6, 8, 10, 12, 24, 48 and 72 h before (0 hour) or after administration. After centrifugation for 5 minutes at 8000 rpm, blood plasma is separated out and placed in anti freezing plastic test tube for storing in refrigerator at −20 C temporarily.

Concentration of APST in blood plasma is tested by LC-MS/MS method. The linearity range of APST testing is 5 to 5000 ng/ml, and the linear is good.

3. Experiment results

Figure 23:
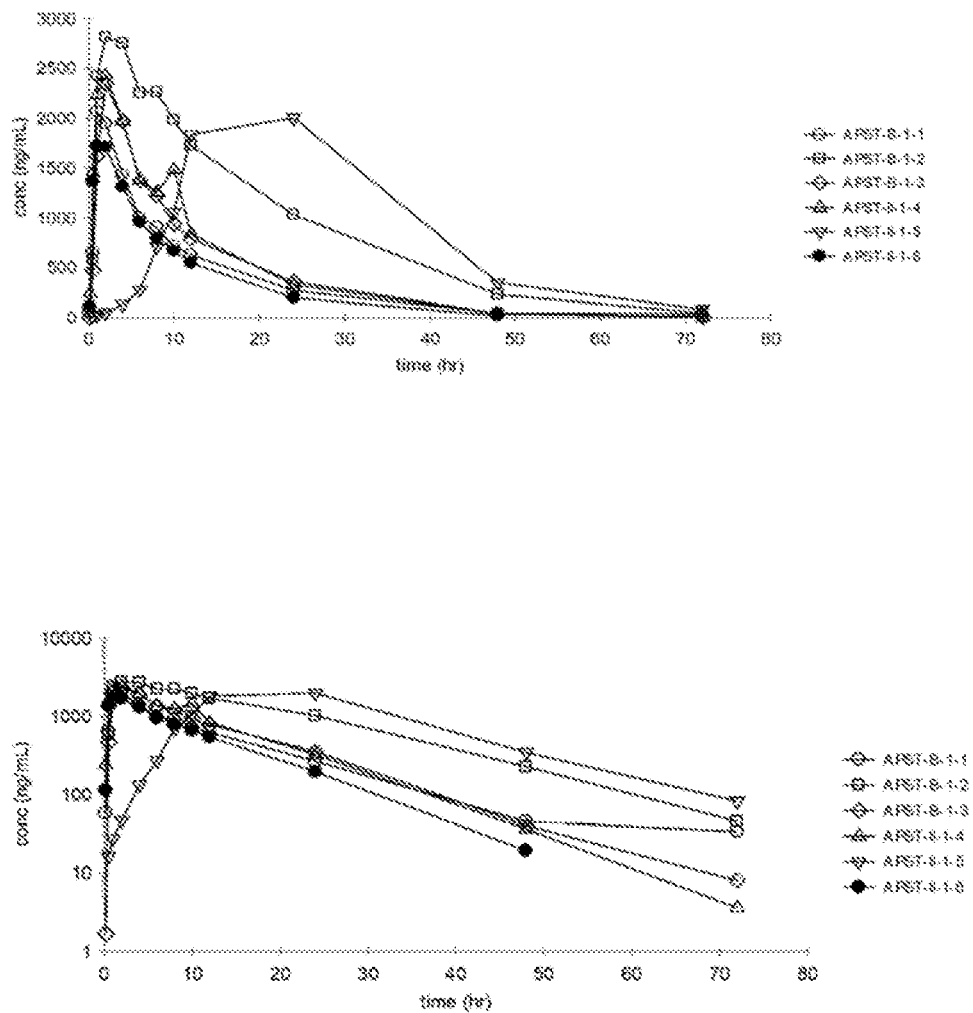
FIG. 23: Plasma concentration-time curve after beagle dogs being given 30 mg APST-B and APST-II capsules of raw material powder through mouth in single period. (Picture above is constant coordinate, picture below is semilogarithm coordinate)

After Beagle dogs being given 30 mg/kg APST-B and APST-II crude drug powder capsule orally respectively, the plasma concentration-time curves are shown in FIG. 23.

4. Analysis of results

Main pharmacokinetic parameters after the Beagle dogs being administrated orally of 30 mg/kg APST-B and APST-II crude drug powder capsules respectively are:

| | APST-B | APST-II |
|---|---|---|
| Tmax | 1.7 ± 0.6 | 9.0 ± 13.0 |
| Cmax | 2405.7 ± 376.6 | 2050.7 ± 356.7 |
| $AUC_{0-t}$ | 38032.5 ± 20537.2 | 37712.7 ± 22408.7 |
| $AUC_{0-\infty}$ | 38497.8 ± 20537.2 | 38210.7 ± 13015.9 |

A t test is carried out after a logarithmic conversion of pharmacokinetic parameters $C_{max}$ and $AUC_{0-t}$. There is no significant meaning (p>0.05) in difference of APST-B and APST-II (p>0.05).

What is claimed is:

1. An Apremilast crystalline Form II of Formula I,

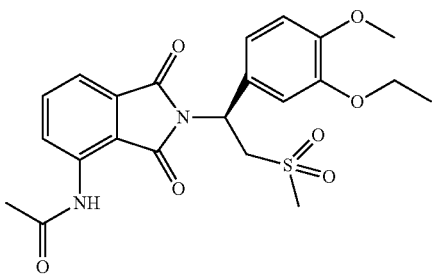

characterized in that:
i) it has an X-ray powder diffraction pattern (XRPD) comprising the following characterizing absorption peaks at 10.6, 11.2, 12.5, 13.2, 13.5, 13.8, 14.7, 16.2, 17.9, 18.7, 20.2, 20.7, 21.5, 21.9, 22.7, 23.1, 25.2, 25.6, 26.5, 27.0, 27.5, 28.2, 29.1, 29.6, 30.9, 32.0, 33.0, 33.5, 34.2, 34.9, 36.2, 39.6, 40.3, 41.0, 43.8 2θ±0.2;
ii) its differential scanning calorimetry (DSC) shows only one endothermic peak at 150±3° C. between 100-180° C.;
iii) its thermal gravimetric analysis (TG) shows that it does not comprise crystallization solvent;
iv) it has a melting temperature between 146-151° C.

2. The Apremilast crystalline Form II of claim 1, characterized in that it has an X-ray powder diffraction pattern (XRPD) comprising the following characterizing absorption peaks at 11.2, 13.2, 13.5, 13.8, 14.7, 16.2, 17.9, 18.7, 20.2, 20.7, 27.0 2θ±0.2.

3. The Apremilast crystalline Form II of claim 1, characterized in that it has an X-ray powder diffraction pattern (XRPD) comprising the following five characterizing absorption peaks at 11.2, 13.2, 13.5, 13.8, 14.7 2θ±0.2.

4. The Apremilast crystalline Form II of claim 1, characterized in that it has an X-ray powder diffraction pattern (XRPD) comprising the following two characterizing absorption peaks at 11.2, 14.7 2θ±0.2.

5. The Apremilast crystalline Form II of claim 1, characterized in that it has similar X-ray powder diffraction pattern (XRPD) as shown in FIG. 2, FIG. 5, FIG. 6, FIG. 8, FIG. 12, FIG. 14, FIG. 16, or FIG. 17.

6. A method for preparing the Apremilast crystalline Form II of claim 1, characterized in using a solvent that is a mixture of acetone and water.

7. The method of claim 6, comprising:
i) dissolving Apremilast or solvate thereof in acetone at elevated temperature, then cooling to below 40 ° C.;
ii) slowly adding water in an amount of 0.5-3 times the volumes of acetone under stirring, optionally seeding with Form II, and continue stirring for 30-180min;
iii) adding water in an amount of 2-6 times the volumes of acetone, stirring for 1-24 hr at 10-60° C.; and
iv) filtering and drying to obtain Apremilast crystalline Form II.

8. The method of claim 6, comprising suspending other Apremilast crystals, in acetone/water mixture, heating and stirring for 1-72 h, and cooling, filtering and drying to obtain Apremilast crystalline Form II.

9. A pharmaceutical composition comprising an Apremilast crystalline Form II of claim 1 as an active pharmaceutical ingredient and a pharmaceutically acceptable carrier.

10. The pharmaceutical composition of claim 9, characterized in that the active pharmaceutical ingredient comprises 1-100% of Apremilast crystalline Form II.

* * * * *